(12) United States Patent
Marhold et al.

(10) Patent No.: US 7,268,260 B2
(45) Date of Patent: Sep. 11, 2007

(54) FLUORINE-CONTAINING BISPHENOLS, THEIR PREPARATION, THEIR PRECURSORS AND INTERMEDIATES, AND USE OF THE FLUORINE-CONTAINING BISPHENOLS

(75) Inventors: Albrecht Marhold, Leverkusen (DE); Käthe Baumann, Wuppertal (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

(21) Appl. No.: 11/498,421

(22) Filed: Aug. 3, 2006

(65) Prior Publication Data
US 2006/0266985 A1   Nov. 30, 2006

Related U.S. Application Data

(62) Division of application No. 11/151,249, filed on Jun. 13, 2005, now Pat. No. 7,112,704, which is a division of application No. 10/157,520, filed on May 29, 2002, now Pat. No. 6,936,739.

(30) Foreign Application Priority Data
May 31, 2001   (DE) ................. 101 26 432

(51) Int. Cl.
  *C07C 39/12*  (2006.01)
(52) U.S. Cl. .................................... 568/729
(58) Field of Classification Search ............ None
  See application file for complete search history.

(56) References Cited

U.S. PATENT DOCUMENTS

| 3,431,343 A | 3/1969 | Stecker | 424/347 |
| 4,168,388 A | 9/1979 | Lavagnino | 568/647 |

FOREIGN PATENT DOCUMENTS

| JP | 5-170892 | 7/1993 |
| JP | 05331084 A | * 12/1993 |
| JP | 2000-273166 | 10/2000 |
| WO | 8202381 A | 7/1982 |
| WO | 0248081 | 6/2002 |

OTHER PUBLICATIONS

Polym. Mater. Sci. Eng., 74, (month unavailable) 1996, pp. 133-134, Hilmar Köner et al, "Tuning Physical Properties and Mesophase Behavior in Liquid Crystalline Thermoset Mixtures".
Organic Preparation and Procedures Int., 11(1), (month unavailable) 1979, pp. 23-26, E.R. Lavagnino et al, "A General Method For the Preparation of Hydroxybenzotrifluorides".
Topic in Applied Chemistry: Fluoropolymers, (month unavailable) 1999 (1), pp. 127-150, Shigeo Nakamura et al, "Synthesis and Properties of Fluorine-Containing Aromatic Condensation Polymers Obtained from Bisphenol AF and its Derivatives".
J. Gen Chem. USSR (Engl. Transl.) 35, (month unavailable) 1965, pp. 1616-1623, L.M. Yagupol'skii et al, "α,α,α'α',-Tetrafluorobibenzyl Derivates IV. Amino Derivatives of α,α,α'α'-Tetrafluorobibenzyl".
Polymer, vol. 38, No. 14, (month unavailable) 1997, pp. 3669-3676, E-Joon Choi et al, "Synthesis, thermal and radiation sensitivites of fluorine containing methylene-bridged aromatic polyesters".

* cited by examiner

Primary Examiner—Thurman K Page
Assistant Examiner—Kellette Gale
(74) Attorney, Agent, or Firm—Michael A. Miller

(57) ABSTRACT

This invention relates to 1,2-di(4-hydroxyaryl)tetrafluoroethanes of the general formula (I)

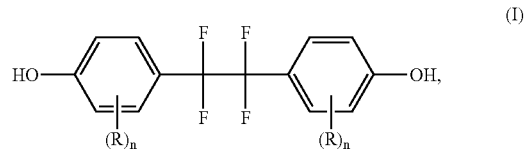

wherein
R are each, independently of one another, hydrogen, F, Cl, Br, I, CN, $COOR^2$, $C_1$-$C_4$-alkyl, $C_1$-$C_4$-alkoxy, $C_1$-$C_4$-alkylthio, $C_1$-$C_4$-perfluoroalkyl, $C_1$-$C_4$-perfluoroalkoxy, $C_1$-$C_4$-perfluoroalkylthio, $C_1$-$C_4$-polyfluoroalkyl, $C_1$-$C_4$-polyfluoroalkoxy, or $C_1$-$C_4$-polyfluoroalkylthio,
$R^2$ is $C_1$-$C_4$-alkyl, and
n is an integer from 0 to 4.

This invention further relates to the preparation of such compounds as well as to precursors and intermediates that can be used in their preparation.

2 Claims, No Drawings

FLUORINE-CONTAINING BISPHENOLS, THEIR PREPARATION, THEIR PRECURSORS AND INTERMEDIATES, AND USE OF THE FLUORINE-CONTAINING BISPHENOLS

RELATED APPLICATIONS

The present invention is a Divisional of application Ser. No. 11/151,249 filed Jun. 13, 2005, now U.S. Pat. No. 7,112,704, which is a Divisional of application Ser. No. 10/157,520 filed May 29, 2002, now U.S. Pat. No. 6,936,739.

BACKGROUND OF THE INVENTION

The present invention relates to fluorine-containing bisphenols, their preparation, some precursors and intermediates of this preparation, and the use of the fluorine-containing bisphenols as starting materials for the production of liquid crystals, polymers and flame retardants.

Particular fluorine-containing bisphenols are already known as starting materials for the production of liquid crystals (Polym. Mater. Sci. Eng., 1996, 74, 133-134) or as monomers for polymerization (Fluoropolymers, 1999, 1, 127-150), for example for preparing polycarbonate (JP 05170892 A2), polyethers (JP 2000273166 A2), or polyesters (Polymer, 1997, 38, 3669-3676). It is also known that in the case of liquid crystals it is advantageous for these to have a linear molecular structure (C. Weygand, "Chemische Morphologie der Flüssigkeiten", Handbuch und Jahrbuch der chemischen Physik, Volume 2, section 3c, Leipzig, Akadem. Verlagsges. 1941; H.-G. Elias, Makromoleküle, 5th edition, Volume 1, chapter 20, section 20.1.2, Hüthig & Wepf Verlag, Basle 1990).

J. Gen. Chem. USSR (Engl. Transl.), 1965, 35, 1616-1623, discloses that various 1,2-di(4-halophenyl)tetrachloroethanes (B) can be prepared by cross-coupling of 4-halobenzotrichlorides (A) by means of copper in pyridine. In addition to the desired 1,2-di(4-halophenyl)tetrachloroethanes of the formula (B), this process also gives significant amounts of 1,2-di(4-halophenyl)dichloro-ethylenes of the formula (C). A disadvantage is that these compounds of the formula (C) cannot be fluorinated directly to form the corresponding 1,2-di(4-halophenyl)tetrafluoroethanes, which leads to costly losses in yield.

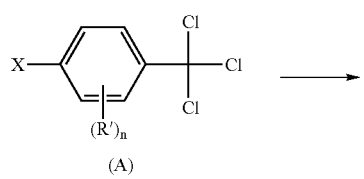

(A)

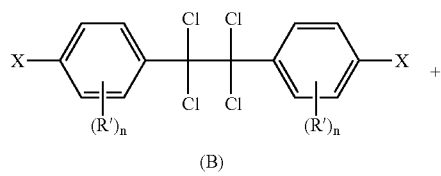

(B)

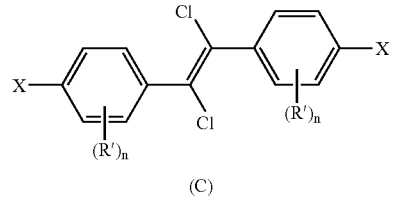

(C)

According to J. Gen. Chem. USSR (Engl. Transl.), 1965, 35, 1616-1623, fluorination of 1,2-di(4-halophenyl)tetrachloroethane of the formula (B) to 1,2-di(4-halophenyl)tetrafluoroethane (C) is possible only by using the highly toxic and expensive antimony(III) fluoride and a catalyst at high temperatures.

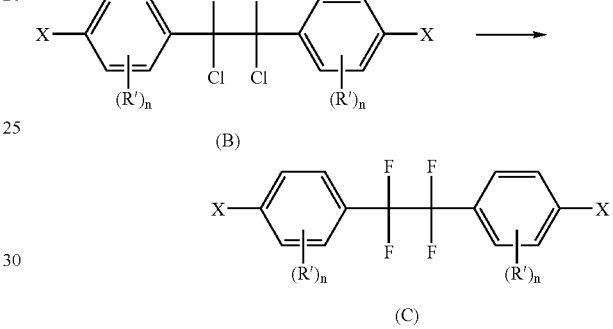

(B)

(C)

U.S. Pat. No. 4,168,388 discloses a process for preparing 2-, 3-, and 4-trifluoromethylphenol from the corresponding 2-, 3-, and 4-trifluoro-methylchlorobenzene. It has the disadvantage that sodium hydride, which ignites readily and reacts vigorously with water, is used as base. In addition, it has been found that the solvent N,N-dimethylacetamide that is used decomposes to form the corrosive N,N-dimethylamine under the reaction conditions described. This prevents recycling of the solvent and makes the process expensive.

Due to the increasing demand for liquid crystals, it is an object of the present invention to provide new fluorine-containing bifunctional compounds having a linear molecular structure.

SUMMARY OF THE INVENTION

This object is achieved with 1,2-di(4-hydroxyaryl)tetrafluoroethanes of the general formula (I)

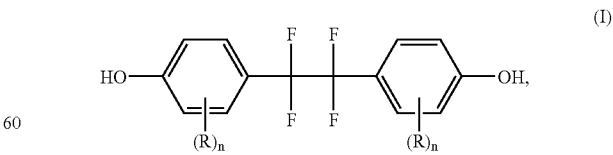

(I)

wherein

R are each, independently of one another, hydrogen, F, Cl, Br, I, CN, COOR$^2$, C$_1$-C$_4$-alkyl, C$_1$-C$_4$-alkoxy, C$_1$-C$_4$-alkylthio, C$_1$-C$_4$-perfluoroalkyl, C$_1$-C$_4$-perfluoroalkoxy, $C_1$-$C_4$-perfluoroalkylthio, $C_1$-$C_4$-polyfluoroalkyl, $C_1$-$C_4$-polyfluoroalkoxy, or $C_1$-$C_4$-polyfluoroalkylthio, $R^2$ is $C_1$-$C_4$-alkyl, and n is an integer from 0 to 4.

DETAILED DESCRIPTION OF THE INVENTION

Preference is given to compounds of the general formula (I) in which

R are each, independently of one another, hydrogen, F, Cl, Br, methyl, methoxy, trifluoromethyl, or trifluoromethoxy, and n is 0 or 1.

As compounds of the general formula (I), particular preference is given to 1,2-di(4-hydroxyphenyl)tetrafluoroethane, 1,2-di(3-chloro-4-hydroxyphenyl)tetrafluoroethane, 1,2-di(3-fluoro-4-hydroxyphenyl)tetra-fluoroethane, 1,2-di(3-bromo-4-hydroxyphenyl)tetrafluoroethane, and 1,2-di(3-methyl-4-hydroxyphenyl)tetrafluoroethane.

The invention also provides a process for preparing the compounds of the general formula (I) comprising subjecting to an ether cleavage compounds of the general formula (VI)

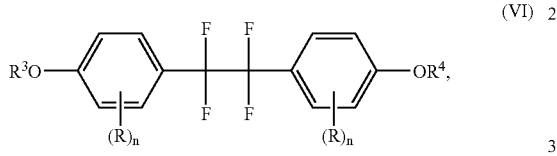

(VI)

where $R^3$ and $R^4$ are identical or different and are each benzyl, substituted benzyl (preferably 1-($C_1$-$C_4$-alkyl)benzyl), benzhydryl, substituted benzhydryl, isopropyl, tert-butyl, or cyclohexyl, and R and n are as defined in the general formula (I).

The ether cleavage of these 1,2-di(4-alkoxyphenyl)tetrafluoro-ethanes of the formula (VI) is carried out either by a hydrogenation or a cleavage in acid medium. When $R^3$ and/or $R^4$ are a benzyl radical or a substituted benzyl radical, hydrogenation has been found to be particularly useful, whereas cleavage in acid medium is the preferred variant for all other meanings of $R^3$ and $R^4$. Both the hydrogenation and the cleavage in acid medium can be carried out by methods known in the art. For the cleavage in acid medium, use is usually made of aqueous acids such as HCl, HBr, $H_2SO_4$, acetic acid, or phosphoric acid. The hydrogenation is carried out using hydrogen and conventional hydrogenation catalysts such as supported or unsupported noble metal catalysts. For example, palladium on activated carbon in an organic solvent such as ethanol is suitable.

The compounds of the general formula (VI) have not hitherto been known. The invention therefore also provides the compounds of the general formula (VI)

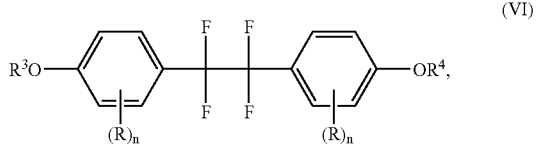

(VI)

where $R^3$ and $R^4$ are identical or different and are each benzyl, substituted benzyl (preferably 1-($C_1$-$C_4$-alkyl)benzyl), benzhydryl, substituted benzhydryl, isopropyl, tert-butyl, or cyclohexyl, and R and n are as defined in the general formula (I).

The compounds of the general formula (VI) can be obtained by etherification using the appropriate alcohols.

The invention therefore additionally provides a process for preparing compounds of the general formula (VI) comprising reacting compounds of the general formula (V)

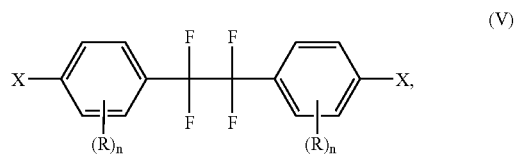

(V)

where X is a halogen or pseudohalogen and R and n are as defined for the general formula (I), with an alcohol of the formula $R^3OH$ and/or an alcohol of the formula $R^4OH$, where $R^3$ and $R^4$ are as defined for the general formula (VI). In this process, preference is given to using compounds of the general formula (V) in which X is fluorine or chlorine. As alcohol, preference is given to using benzyl alcohol.

This reaction of the 1,2-di(4-halophenyl)tetrafluoroethane of the general formula (V) to form the 1,2-di(4-alkoxyphenyl)tetrafluoroethane of the general formula (VI) is usually carried out in the presence of an inorganic base in a polar aprotic solvent.

The inorganic base can be, for example, a hydroxide, carbonate, hydrogen sulfate, sulfate, hydrogen phosphate, or phosphate of an alkali metal or alkaline earth metal. Preference is given to using potassium hydroxide.

The polar aprotic solvent can, according to the invention, be an amide such as N,N-dimethylacetamide or N-methylpyrrolidone, a sulfoxide such as dimethyl sulfoxide, a sulfone such as tetramethylene sulfone, or a nitrile such as acetonitrile. Preference is given to using N-methylpyrrolidone. The reaction can, if desired, be carried out in the presence of water.

At the end of the reaction, some or all of the solvent can be recovered by distillation (possibly as a mixture with the water formed in the reaction). Aqueous N-methylpyrrolidone can, for example, be reused a number of times in further batches of this process step, without drying being necessary. Thus, when using potassium hydroxide as base, the waste products of this reaction can be restricted to potassium chloride.

After the reaction is complete and the solvent has been distilled off, the product obtained in this way can be purified by, for example, recrystallization or stirring in a suitable solvent, filtration, and drying.

The compounds of the general formula (V) can be prepared by fluorination of the corresponding chlorinated compounds.

Accordingly, the invention further provides a process for preparing compounds of the general formula (V) comprising reacting compounds of the general formula (III)

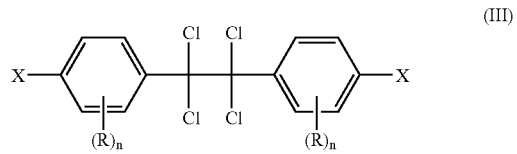

(III)

with anhydrous hydrofluoric acid.

Here, use is usually made of from 4 to 50 mol of anhydrous hydrofluoric acid per mol of compound (III). The material that is commercially available under the name "anhydrous hydrofluoric acid" is sufficiently free of water for this purpose.

The fluorination can, for example, be carried out at temperatures of 0 to 180° C. and a pressure in the range 1 to 50 bar. Preference is given to temperatures of 10 to 160° C. and a pressure of 10 to 30 bar. If appropriate, the reaction is carried out in the presence of a catalyst and/or an inert solvent. Examples of catalysts that can be used are boron trifluoride, titanium tetrachloride, and antimony pentachloride and pentafluoride. Dichloromethane has been found to be useful as solvent.

It is possible for the anhydrous hydrofluoric acid to be placed in a reaction vessel and the compound (III) to be added, or the procedure can be reversed. It is advantageous to combine the hydrofluoric acid and the compound (III) at relatively low temperatures within the abovementioned temperature ranges (e.g., up to 50° C.) and then to increase the temperature stepwise. If desired, the excess anhydrous hydrofluoric acid can be recovered virtually completely by distillation.

After the reaction is complete and the excess anhydrous hydrofluoric acid has been distilled off, the reaction mixture can be recrystallized or admixed with a suitable solvent (e.g., dichloromethane). In this form of work-up, the organic phase is subsequently admixed with activated carbon and/or an alkali metal fluoride, filtered and evaporated or subjected to an aqueous work-up. The resulting 1,2-di(4-halophenyl) tetrafluoroethane product of the general formula (V) can be purified by, for example, recrystallization or stirring in a suitable solvent, filtration, and drying.

This process differs from the process known from J. Gen. Chem. USSR (Engl. Transl.), 1965, 35, 1616-1623, in that hydrofluoric acid is used in place of large amounts of antimony trifluoride and antimony trifluoride is at most optionally added in very small amounts as catalyst. This makes it possible for the process to be carried out significantly more simply in terms of safety precautions and in an economically attractive manner.

The compounds of the general formula (III) can be prepared by reaction of benzotrichlorides of the general formula (II)

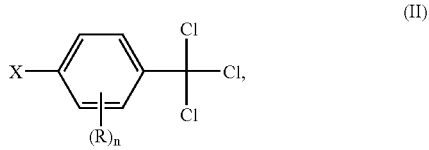

where

R and n are as defined for the general formula (I), and

X is a halogen or pseudohalogen, in the presence of copper and in a tertiary amine as solvent.

This reaction is a cross-coupling of the benzotrichlorides of the general formula (II). Pyridine is preferably used as solvent.

Preference is given to using benzotrichlorides of the general formula (I) in which X is fluorine, chlorine, or nitro. Particular preference is given to benzotrichlorides of the general formula (I) in which X is fluorine or chlorine. In particular, use is made of 4-fluorobenzotrichloride, 4-chlorobenzotrichloride, 3,4-dichlorobenzotrichloride, or 3-trifluoromethyl-4-chlorobenzotrichloride.

The copper can be used in the form of powder or turnings. The reaction is carried out using a molar ratio of copper to benzotrichloride of the general formula (II) of (0.4 to 5):1, preferably (0.4 to 1):1, and particularly preferably 0.5:1. The reaction temperature is usually in the range from 0 to 115° C. The reaction is preferably carried out in the range from 40 to 80° C.

In this cross-coupling, the benzotrichlorides of the general formula (II) form a reaction mixture that contains 1,2-di(4-halophenyl)tetrachloroethanes of the general formula (III)

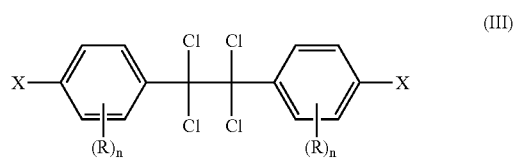

and possibly 1,2-di(4-halophenyl)dichloroethylenes of the general formula (IV)

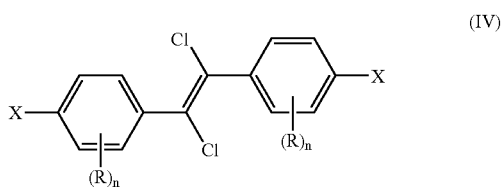

The work-up of this mixture can be carried out, for example, by pouring it into ice water, filtering the mixture, slurrying the precipitate with water, washing the precipitate free of base (e.g., with aqueous hydrogen chloride solution), filtering it off, and drying it. If appropriate, the product mixture obtained in this way can be purified by washing with an inert solvent (e.g., cyclohexane or methanol) or by recrystallization. However, other known methods can also be utilized for the work-up.

The cross-coupling of the first step of the process of the invention may be followed by a chlorination of the resulting product mixture. By means of this chlorination, any 1,2-di (4-halophenyl)dichloroethylenes of the general formula (IV) present in the reaction mixture can be converted into the desired 1,2-di(4-halophenyl)tetrachloroethanes of the formula (III).

For this purpose, the crude reaction mixture from the cross-coupling, the evaporated residue after washing with an inert solvent or the evaporated mother liquor after crystallization can be chlorinated to obtain the compounds of the formula (III) in high yield and purity. The chlorination of the mixture in a suitable solvent (preferably chloroform, chlorobenzene, or chlorobenzotrichloride) is carried out by methods of the prior art. The product obtained in this way can be purified by, for example, recrystallization or stirring in a suitable solvent, filtration, and drying.

The invention further provides the compounds of the general formula (IV)

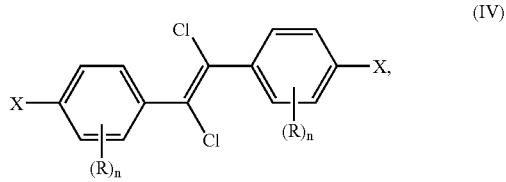

where
X is fluorine, and
R and n are as defined for the general formula (I).

The compounds of the general formula (IV) can be isolated from the product mixture of (III) and (IV) by, for example, distillation.

In a preferred embodiment, the preparation of the compounds of the general formula (I) is carried out by means of the following process sequence:
(1) a benzotrichloride of the general formula (II) is reacted in the presence of copper and in a tertiary amine as solvent,
(2) a reaction with anhydrous hydrofluoric acid is subsequently carried out,
(3) an etherification with one or more alcohols of the formula $R^3OH$ and/or $R^4OH$ is then carried out, and
(4) finally, an ether cleavage is carried out to give the compounds of the general formula (I).

This process for preparing the compounds of the general formula (I) gives high yields, uses readily available starting materials, and forms small amounts of waste products.

The invention additionally provides for the use of compounds of the general formula (I) as monomers for preparing polymers (preferably polyesters, polyethers, or polycarbonates) and as starting materials for producing liquid crystals or flame retardants.

The following examples further illustrate details for the preparation and use of the compounds of this invention. The invention, which is set forth in the foregoing disclosure, is not to be limited either in spirit or scope by these examples. Those skilled in the art will readily understand that known variations of the conditions and processes of the following preparative procedures can be used to prepare these compounds. Unless otherwise noted, all temperatures are degrees Celsius and all percentages are percentages by weight.

EXAMPLES

Example 1

(Reaction Using 4-fluorobenzotrichloride)

3700 g of 4-fluorobenzotrichloride together with 14 liters of pyridine were placed in a reaction vessel and, at 65° C., 565 g of copper powder were added a little at a time over a period of 6.5 hours. The mixture was stirred for 16 hours at 65-70° C. A further 100 g of copper powder were added over a period of 1 hour, and the mixture was stirred at 65-70° C. for another 4 hours. The cooled reaction mixture was subsequently poured into 60 liters of ice water, stirred, and filtered with suction. The precipitate was slurried with water, acidified using 1N hydrogen chloride solution, and filtered off with suction, washed with water, and dried at 60° C. in a drying oven.

This gave 2660 g of 1,2-di(4-fluorophenyl)tetrachloroethane in a purity of 84% (GC-% by area), corresponding to a yield of 72% of theory.

To purify the solid further, it was washed twice with 2 liters of cyclohexane and once again filtered off with suction. This gave 1928 g of 1,2-di(4-fluorophenyl)tetrachloroethane as a white solid having a melting point of 128-130° C. This corresponds to a yield of 62% of theory.

Example 2

(Reaction Using 4-Chlorobenzotrichloride)

920 g of 4-chlorobenzotrichloride together with 3200 ml of pyridine were placed in a reaction vessel and, at 65-70° C., 128 g of copper powder were added a little at a time. The mixture was stirred at 70° C. for 19 hours. The cooled reaction mixture was subsequently poured into 15 liters of ice water, stirred, and filtered with suction. The precipitate was slurried with water, acidified using 1N hydrogen chloride solution, and filtered off with suction, washed with water, and dried at 60° C. in a drying oven.

This gave 587 g of 1,2-di(4-chlorophenyl)tetrachloroethane as a white solid having a melting point of 180-187° C. This corresponds to a yield of 75% of theory.

Example 3

(Reaction Using 3,4-dichlorobenzotrichloride)

794 g of 3,4-dichlorobenzotrichloride together with 2400 ml of pyridine were placed in a reaction vessel and 96 g of copper powder were added at room temperature. The mixture was stirred at 65-70° C. for 17 hours. The cooled reaction mixture was subsequently poured into 10 liters of ice water, stirred, and filtered with suction. The precipitate was slurried with water, acidified using 1N hydrogen chloride solution, and filtered off with suction, washed with water, and dried at 60° C. in a drying oven. The resulting solid was recrystallized from toluene.

This gave 305 g of 1,2-di(3,4-dichlorophenyl)tetrachloroethane as a white solid having a melting point of 197-198° C. This corresponds to a yield of 44% of theory.

Example 4

(Reaction Using 3-trifluoromethyl-4-chlorobenzotrichloride)

The procedure of Example 3 was repeated using 3-trifluoromethyl-4-chlorobenzotrichloride to give 1,2-di(3-trifluoromethyl-4-chlorophenyl)-tetrachloroethane in a yield of 63%.

Example 5

(Subsequent Chlorination)

4187 g of a mixture of 1,2-di(4-fluorophenyl)dichloroethylene (65%) and 1,2-di(4-fluorophenyl)tetrachloroethane (31%) together with 10.5 liters of chloroform were placed in a reaction vessel. Chlorine gas was passed through the solution, and at the same time the reaction mixture was irradiated at a wavelength of 254 nm and the temperature was increased to 60° C. The mixture was photochlorinated six times for 7-8 hours each time under these conditions. Nitrogen was then passed through the cooled reaction mixture and the mixture was subsequently evaporated.

This gives 4580 g of 1,2-di(4-fluorophenyl)tetrachloroethane in a purity of 87% (GC-% by area), corresponding to a yield of 87% of theory.

To purify the solid further, it was washed twice with cyclohexane and once again filtered off with suction.

This gave 3280 g of 1,2-di(4-fluorophenyl)tetrachloroethane in a purity of 98.6% (GC-% by area) as a white solid. This corresponds to a yield of 71% of theory.

Example 6

(Fluorination Using Anhydrous Hydrofluoric Acid)

600 ml of anhydrous hydrofluoric acid were placed in a stainless steel autoclave at room temperature. 571 g of 1,2-di(4-fluorophenyl)tetrachloroethane were subsequently added. The temperature was increased stepwise to 146° C. and the hydrogen chloride formed was released at 10-35 bar via a reflux condenser (−15° C.). After HCl gas evolution had ceased, the autoclave was depressurized to atmospheric pressure and the excess hydrofluoric acid was distilled off. The residue was dissolved in dichloromethane, admixed with activated carbon, and then filtered. The filtrate was evaporated and then distilled at 16 mbar (boiling point at 16 mbar: 125-126° C.).

This gave 370 g of 1,2-di(4-fluorophenyl)tetrafluoroethane as a white solid having a melting point of 96-97° C. This corresponds to a yield of 80% of theory.

Example 7

(Fluorination Using Anhydrous Hydrofluoric Acid)

1000 ml of anhydrous hydrofluoric acid and 25 ml of antimony(V) chloride were placed in a stainless steel autoclave at room temperature. 1157 g of 1,2-di(4-chlorophenyl)tetrachloroethane were subsequently added. In a manner analogous to Example 5, the temperature was increased stepwise to 140° C. After HCl gas evolution had ceased, the autoclave was depressurized and the excess hydrofluoric acid was distilled off. The residue was recrystallized from petroleum ether.

This gave 467 g of 1,2-di(4-chlorophenyl)tetrafluoroethane as a white solid having a melting point of 88-90° C. This corresponds to a yield of 49% of theory.

Example 8

(Fluorination Using Anhydrous Hydrofluoric Acid)

500 ml of anhydrous hydrofluoric acid and 5 ml of antimony(V) chloride were placed in a stainless steel autoclave at room temperature. 229 g of 1,2-di(3,4-dichlorophenyl)tetrachloroethane were subsequently added. The temperature was increased stepwise to 146° C. After HCl gas evolution had ceased, the autoclave was depressurized and the excess hydrofluoric acid was distilled off. The residue was taken up in toluene, admixed with activated carbon and sodium fluoride, and then filtered. The resulting filtrate was evaporated and then recrystallized from methanol.

This gave 467 g of 1,2-di(3,4-dichlorophenyl)tetrafluoroethane as a white solid having a melting point of 105-107° C. This corresponds to a yield of 49% of theory.

$^1$H-NMR ($d_6$-DMSO, 400 MHz): [δ in ppm] 7.67 (2H, d, J 8.4 Hz), 7.65 (2H, d, J 2.2 Hz), 7.40 (2H, dd, J 8.4 and 2.2 Hz)

$^{19}$F-NMR ($d_6$-DMSO, 376 MHz): [δ in ppm] −111 (4F, s)

MS (EI) 392 (10%) [M$^+$], 195 (100) [$Cl_2C_6H_3$-$CF_2^+$]

Example 9

(Fluorination Using Anhydrous Hydrofluoric Acid)

1000 ml of anhydrous hydrofluoric acid and 30 ml of antimony(V) chloride were placed in a stainless steel autoclave at room temperature. 350 g of 1,2-di(3-trifluoromethyl-4-chlorophenyl)tetrachloroethane were subsequently added. The autoclave was pressurized with nitrogen, the temperature was increased stepwise to 120° C., and the hydrogen chloride formed was released at 10-35 bar via a reflux condenser (−15° C.). After 3 hours, the evolution of HCl gas had ceased, and the autoclave was depressurized and the excess hydrofluoric acid was distilled off at a pressure down to 100 mbar. The residue was poured into water, and the solid was filtered off with suction and dried in a drying oven.

This gave 275 g of 1,2-di(3-trifluoromethyl-4-chlorophenyl)tetra-fluoroethane as a white solid having a melting point of 154-157° C. This corresponds to a yield of 90% of theory.

MS (EI) 458 (3%)[M$^+$], 229 (100)[Cl-$C_6H_3$(—$CF_3$)—$CF_2^+$]

Example 10

(Etherification with Benzyl Alcohol)

216 g of benzyl alcohol together with 1 liter of N,N-dimethylacetamide were placed in a reaction vessel and cooled to 0° C. 336 g of potassium hydroxide powder was added a little at a time at 0-2° C. over a period of 25 minutes. A solution of 290 g of 1,2-di(4-fluorophenyl)tetrafluoroethane in 500 ml of N,N-dimethylacetamide was subsequently added dropwise at 2-14° C. over a period of 45 minutes. The mixture was stirred for 30 minutes at 14-25° C., then for 16 hours at 84-92° C. The resulting suspension was poured into 2 liters of water, the solid was filtered off with suction, washed with water, and dried at 60° C.

This gave 445 g of 1,2-di(4-benzyloxyphenyl)tetrafluoroethane as a white solid having a purity of 93.4% (HPLC-% by area) and a melting point of 206-208° C. This corresponds to a yield of 95% of theory.

$^1$H-NMR ($d_6$-DMSO, 400 MHz): [δ in ppm] 7.62-7.36 (18H, m); 5.33 (4H, s)

$^{19}$F-NMR ($d_6$-DMSO, 376 MHz): [δ in ppm] −109 (4F, s)

MS (CI) 489 (100%) [M+Na$^+$], 447 (83) [M$^+$−F]

When 2 kg of 1,2-di(4-fluorophenyl)tetrafluoroethane were used as starting material, the corresponding procedure gave 3.13 kg of 1,2-di(4-benzyloxyphenyl)tetrafluoroethane as a white solid having a melting point of 206-208° C. This corresponds to a yield of 97% of theory.

Example 11

(Etherification with Benzyl Alcohol)

42.1 g of KOH (85-90% pure, pellets) together with N-methylpyrrolidone (300 ml) were placed in a reaction vessel under a nitrogen atmosphere at room temperature. After 100 ml of N-methylpyrrolidone had been added, the stirrer was switched on. After everything had been added, the mixture was heated to 100° C. 100 g of 1,2-di(3,4-dichlorophenyl)tetrafluoroethane were subsequently added dropwise over a period of 30 minutes, and 26.4 ml of benzyl alcohol were then added dropwise of a period of 10 minutes. The mixture was stirred at 100° C. for another 20 hours, and 180 ml of solvent were then distilled off via a 10 cm Vigreux column. The residue that remained was slurried in 500 ml of water and then filtered off with suction. The solid was washed with water (3 times using 500 ml each time). The residue was dried at 70° C. in a convection oven.

This gave 113.5 g of 1,2-di(3-chloro-4-benzyloxyphenyl) tetrafluoroethane as a white solid. This corresponds to a yield of 83% of theory.

$^1$H-NMR (d$_6$-DMSO, 400 MHz): [δ in ppm] 7.85-7.36 (16H, m) 5.31 (4H, s)

$^{19}$F-NMR (d$_6$-DMSO, 376 MHz): [δ in ppm] –109 (4F, s)

MS (EI): 534 (2%) [M$^+$], 91(100) [C$_6$H$_5$CH$_2$$^+$]

Example 12

(Etherification with Benzyl Alcohol)

36.0 g of KOH (85-90% pure, pellets) together with N-methylpyrrolidone (200 ml) were placed in a reaction vessel under a nitrogen atmosphere at room temperature. After 100 ml of N-methylpyrrolidone had been added, the stirrer was switched on. After everything had been added, the mixture was heated to 100° C. 100 g of 1,2-di(3-trifluoromethyl-4-chlorophenyl)tetrafluoroethane in N-methylpyrrolidone (50 ml) and then 22.5 ml of benzyl alcohol were subsequently added dropwise. The mixture was stirred at 100° C. for another 42 hours, and 90 ml of solvent were then distilled off via a 10 cm Vigreux column. The residue that remained was slurried with water and then filtered off with suction. The solid was washed with water (3×200 ml). The residue was dried at 70° C. in a convection oven.

This gave 49 g of 1,2-di(3-trifluoromethyl-4-benzyloxyphenyl)tetra-fluoroethane as a white solid. This corresponds to a yield of 53% of theory.

$^1$H-NMR (d$_6$-DMSO, 400 MHz): [δ in ppm] 7.83(2H, d, J 9.0 Hz); 7.56-7.36 (16H, m); 5.38 (4H, s)

$^{19}$F-NMR (d$_6$-DMSO, 376 MHz): [δ in ppm] –61 (6F, s), –109 (4F, s)

MS (EI) (1%) [M$^+$], 91 (100) [C$_6$H$_5$CH$_2$$^+$]

Example 13

(Ether Cleavage by Hydrogenation)

2866 g of 1,2-di(4-benzyloxyphenyl)tetrafluoroethane together with 28 liters of ethanol were placed in a hydrogenation vessel and admixed with 280 g of 5% palladium on activated carbon. The vessel was subsequently pressurized with 2-4 bar of hydrogen for 15 hours at 25-30° C. and then depressurized. The mixture was filtered with suction and the filtrate was evaporated.

This gave 1718 g of 1,2-di(4-hydroxyphenyl)tetrafluoroethane as a white solid having a purity of 98.4% (HPLC-% by area) and a melting point of 224-225° C. This corresponds to a yield of 98% of theory.

$^1$H-NMR (d$_6$-DMSO, 400 MHz): [δ in ppm] 7.18 (4H, d, J 8.6); 6.85 (4H, d, J 8.6)

$^{19}$F-NMR (d$_6$-DMSO, 376 MHz): [δ in ppm] –109 (4F, s)

MS (EI) 286 (14%) [M$^+$], 143 (100) [HO-C$_6$H$_4$-CF$_2$$^+$]

Example 14

(Ether Cleavage by Hydrogenation)

113 g of 1,2-di(3-chloro-4-benzyloxyphenyl)tetrafluoroethane together with 500 ml of ethanol were placed in a hydrogenation vessel and admixed with 1 g of 5% palladium on activated carbon. The vessel was subsequently pressurized with 2-4 bar of hydrogen for 30 hours at 25-30° C. and then depressurized. The mixture was filtered hot and the filtrate was evaporated.

This gave 45 g of 1,2-di(3-chloro-4-hydroxyphenyl)tetrafluoroethane as a white solid. This corresponds to a yield of 60% of theory.

$^{19}$F-NMR (d$_6$-DMSO, 376 MHz): [δ in ppm] –110 (4F, s)

MS (Cl) 355 (100%) [M+H$^+$]

Example 15

(Ether Cleavage by Hydrogenation)

100 g of 1,2-di(3-trifluoromethyl-4-benzyloxyphenyl)tetrafluoroethane together with 500 ml of ethanol were placed in a hydrogenation vessel and admixed with 1 g of 5% palladium on activated carbon. The vessel was subsequently pressurized with 2-4 bar of hydrogen for 10 hours at 25-30° C. and then depressurized. The mixture was filtered and the filtrate was evaporated.

This gave 29 g of 1,2-di(3-trifluoromethyl-4-hydroxyphenyl)tetra-fluoroethane as a white solid having a purity of 98.9% (GC-% by area). This corresponds to a yield of 85% of theory.

$^1$H-NMR (d$_6$-DMSO, 400 MHz): [δ in ppm] 11.45 (2H, s); 7.58 (2H, d, J 8.6 Hz); 7.38 (2H, s); 7.20 (2H, d, J 8.6 Hz)

$^{19}$F-NMR (d$_6$-DMSO, 376 MHz): [δ in ppm] –61 (6F, s), –110 (4F, s)

MS (EI) 422 (12%) [M$^+$], 211 (100) [HO-C$_6$H$_3$(—CF$_3$)-CF$_2$$^+$]

What is claimed is:

1. A compound of formula (VI)

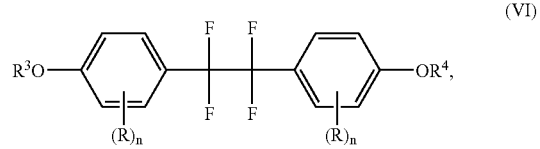

wherein
R$^3$ and R$^4$ are identical or different and are each benzyl, substituted benzyl, benzhydryl, substituted benzhydryl, isopropyl, tert-butyl, or cyclohexyl, and
R are each, independently of one another, hydrogen, F, Cl, Br, I, CN, COOR$^2$, C$_1$-C$_4$-alkyl, C$_1$-C$_4$-alkoxy, C$_1$-C$_4$-alkylthio, C$_1$-C$_4$-perfluoroalkyl, C$_1$-C$_4$-perfluoroalkoxy, C$_1$-C$_4$-perfluoroalkylthio, C$_1$-C$_4$-polyfluoroalkyl, C$_1$-C$_4$-polyfluoroalkoxy, or C$_1$-C$_4$-polyfluoroalkylthio, and
n is an integer from 0 to 4;
wherein
R$^2$ is C$_1$-C$_4$-alkyl.

2. A process for preparing a compound according to Claim 1 comprising reacting a compound of formula (V)

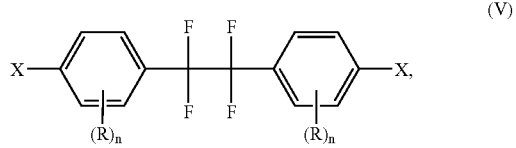

wherein
X is a halogen or pseudohalogen,
R are each, independently of one another, hydrogen, F, Cl, Br, I, CN, COOR$^2$, C$_1$-C$_4$-alkyl, C$_1$-C$_4$-alkoxy, C$_1$-C$_4$-alkylthio, C$_1$-C$_4$-perfluoroalkyl, C$_1$-C$_4$-perfluoroalkoxy, $C_1$-$C_4$-perfluoroalkylthio, $C_1$-$C_4$-polyfluoroalkyl, $C_1$-$C_4$-polyfluoroalkyl, $C_1$$C_4$-polyfluoroalkoxy, or $C_1$-$C_4$-polyfluoroalkylthio, and n is an integer from 0 to 4, with an alcohol of the formula $R^3OH$, wherein $R^3$ is benzyl, substituted benzyl, benzhydryl, substituted benzhydryl, isopropyl, tert-butyl, or cyclohexyl, and/or an alcohol of the formula $R^4OH$, wherein $R^4$ is benzyl, substituted benzyl, benzhydryl, substituted benzhydryl, isopropyl, tert-butyl, or cyclohexyl.

* * * * *